United States Patent [19]
MacMicking et al.

[11] Patent Number: 5,850,004
[45] Date of Patent: Dec. 15, 1998

[54] TRANSGENIC MOUSE DEFICIENT IN INDUCIBLE NITRIC OXIDE SYNTHASE

[75] Inventors: John MacMicking, New York; Carl Nathan, Larchmont, both of N.Y.; John S. Mudgett, Scotch Plains, N.J.

[73] Assignees: Cornell Research Foundation, Inc., Ithaca, N.Y.; Merck & Co., Inc., Rahway, N.J.

[21] Appl. No.: 808,191

[22] Filed: Feb. 28, 1997

Related U.S. Application Data

[63] Continuation of Ser. No. 284,898, Aug. 2, 1994, abandoned.
[51] Int. Cl.$^6$ .............................. C12N 5/00; C12N 15/00; A61K 49/00
[52] U.S. Cl. ..................... 800/2; 800/DIG. 1; 435/172.3; 435/320.1; 424/9.2
[58] Field of Search .................................. 800/2, DIG. 1; 435/172.3, 320.1; 424/9.2

[56] References Cited

PUBLICATIONS

Mansour et al (1988) Nature 336, 348–352.
Alberts et al Molec. Biol. of the Cell, 188–189, 1983.
Geller et al (1993) Proced. Nat. Acad. Sci. 90, 3491–3495.
Huang et al (1993) Cell 75, 1273–1286.
Xie et al (1992) Science 256, 225–228.
Flynn, J. L., et al., "Major histocompatibility complex class I–restricted T cells are required for resistance to *Mycobacterium tuberculosis* infection," *Proc. Natl. Acad. Sci. USA*, vol. 89, pp. 12013–12017, Dec. 1992.
Kulkarni, A. B., et al., "Transforming growth factor $\beta_1$ null mutation in mice causes excessive inflammatory response and early death," *Proc. Natl. Acad. Sci. USA*, vol. 90, pp. 770–774, Jan. 1993.
Dalton, D. K., et al., "Multiple Defects of Immune Cell Function in Mice with Disrupted Interferon–γ Genes," *Science*, vol. 259, pp. 1739–1742, 19 Mar. 1993.
Huang, S., et al., "Immune Response in Mice That Lack the Interferon–γ Receptor," *Science*, vol. 259, pp. 1742–1745, 19 Mar. 1993.
Kamijo, R., et al., "Requirement for Transcription Factor IRF–1 in NO Synthase Induction in Macrophages," *Science*, vol. 263, pp. 1612–1615, 18 Mar. 1994.
Apasov, S., et al., "Highly lytic CD8$^+$, αβ T–cell receptor cytotoxic T cells with major histocompatibility complex (MHC) class I antigen–directed cytotoxicity in $\beta^2$–microglobulin, MHC class I–deficient mice," *Proc. Natl. Acad. Sci. USA*, vol. 90, pp. 2837–2841, Apr. 1993.
Denis, M., "Tumor Necrosis Factor and Granulocyte Macrophage–Colony Stimulating Factor Stimulate Human Macrophages to Restrict Growth of Virulent *Mycobacterium avium* and to Kill Avirulent *M. avium*: Killing Effector Mechanism Depends on the Generation of Reactive Nitrogen Intermediates," *Journal of Leukocyte Biology*, vol. 49, pp. 380–387 (1991).
North, J., et al., "Microbacterial Virulence, Virulent Strains of *Mycobacteria tuberculosis* Have Faster In Vivo Doubling Times and Are Better Equipped to Resist Growth–inhibiting Functions of Macrophages in the Presence and Absence of Specific Immunity," *J. Exp. Med.*, vol. 177, pp. 1723–1733, Jun. 1993.
Stuehr, D.J., et al., "Mammalian nitrate biosynthesis: Mouse macrophages produce nitrite and nitrate in response to *Escherichia coli* lipopolysaccharide," *Proc. Natl. Acad. Sci. USA*, vol. 82, pp. 7738–7742, Nov. 1985.

*Primary Examiner*—Deborah Crouch
*Attorney, Agent, or Firm*—Nixon, Hargrave, Devans & Doyle LLP

[57] ABSTRACT

The present invention provides an inducible nitric oxide synthase ("iNOS")-deficient transgenic mouse, novel replacement vectors designed for the disruption of the iNOS gene, embryonic stem (ES) cells which are singly allelic relative to the deficient iNOS locus, a host cell line or cell clone carrying a congenitally altered iNOS gene, and a method of producing such a transgenic mouse.

The iNOS-deficient transgenic mice can be used to evaluate and/or test their susceptibility to infectious or tumorigenic challenge, autoimmunity, septic shock and inflammatory and allergic diseases.

13 Claims, 4 Drawing Sheets

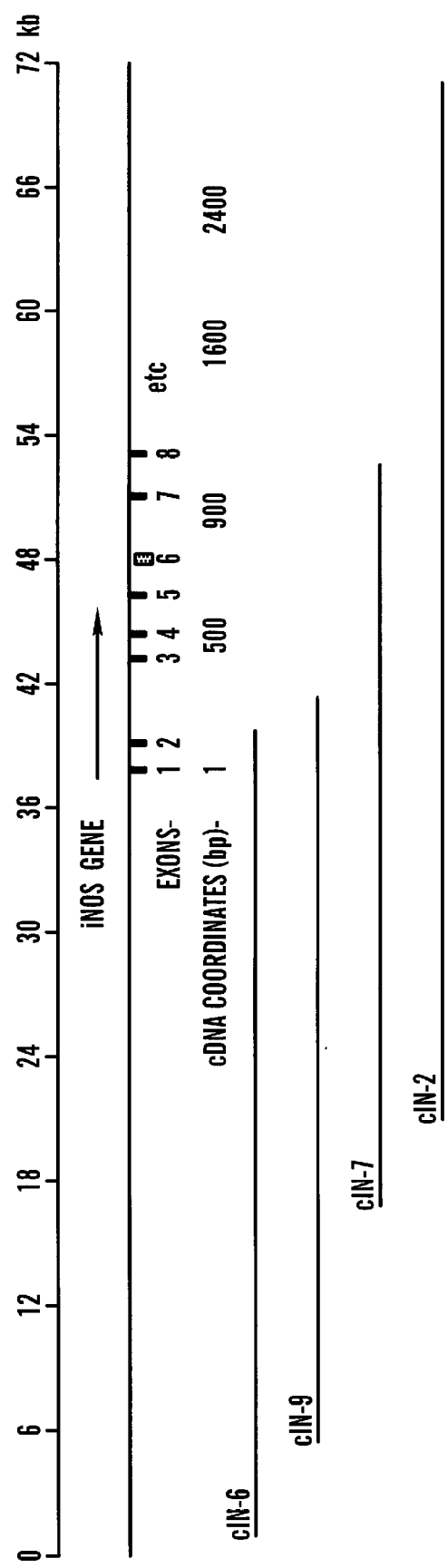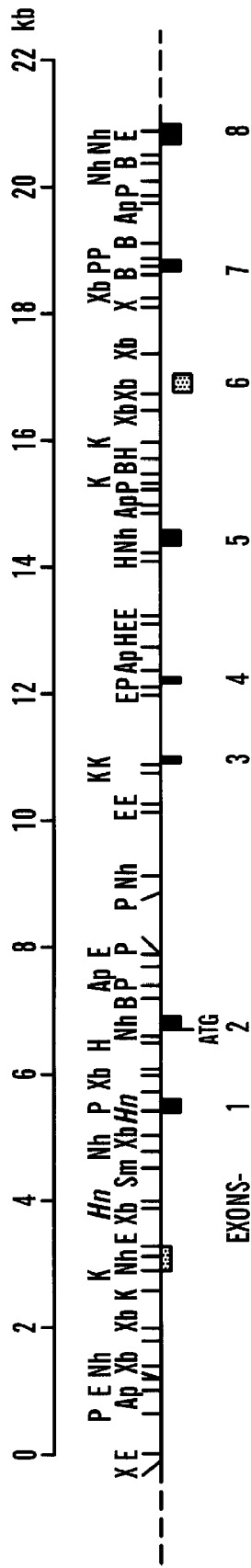
FIG. 3A
FIG. 3B

TRANSGENIC MOUSE DEFICIENT IN INDUCIBLE NITRIC OXIDE SYNTHASE

This application is a continuation of application Ser. No. 08/284,898 filed Aug. 2, 1994 abandoned.

This invention was made with partial Government support under Grant Nos. HL51967 and AI34543 from the National Institutes of Health. The Government has certain rights in this invention.

FIELD OF THE INVENTION

The present invention relates generally to a transgenic mouse. More particularly, the present invention relates to an inducible nitric oxide synthase ("iNOS")deficient transgenic mouse, novel replacement vectors designed for the disruption of the iNOS gene, embryonic stem (ES) cells which are singly allelic relative to the deficient iNOS locus, a host cell line or cell clone carrying a congenitally altered iNOS gene, and to a method of producing such a transgenic mouse. Above and hereinafter, "deficient" means altered to such an extent as to give a phenotype discernibly different from wild type.

BACKGROUND OF THE INVENTION

1. The Nitric Oxide System

Nearly every field of physiology has been reevaluated in the last few years in the light of evidence for the widespread production and servoregulatory role of a tiny, reactive, inorganic, radical gas, nitric oxide ("NO"). Produced in small amounts under physiologic conditions by endothelium and neurons, NO appears to relax smooth muscle and hence regulate blood pressure and bronchial tone, inhibit the adhesion of platelets and neutrophils, and transmit nonadrenergic, non-cholinergic neural impulses. A distinct set of functions is attributable to NO when produced in much larger amounts by macrophages and other cells after exposure to cytokines or microbial products. The provision of NO for such tasks is generated biologically by the enzyme, nitric oxide synthase ("NOS"), which utilizes arginine and molecular oxygen as co-substrates.

2. Nitric Oxide Synthase

Smooth muscle tone and neural signaling are regulated by two constitutive, calmodulin-and $Ca^{2+}$-dependent constitutive nitric oxide synthase ("cNOS"). In contrast, high-output production of NO is achieved by gamma interferon ("IFN-γ") and bacterial lipopolysaccharide ("LPS") inducible nitric oxide synthase ("iNOS"), so denoted for its inducibility and independence of exogenous calmodulin and elevated $Ca^{2+}$. It is noted that in some literature an alternative definition for "iNOS" comprises independence of elevated calcium ion ($Ca^{2+}$) above the level in resting cells and independence of exogenous calmodulin. Induction of iNOS is largely transcriptional (Xie et al., 1992, *Science*, vol. 256, pp. 225–228; and Xie et al., 1993, *J. Exp. Med., vol.* 177, pp. 1779–1784); its suppression by TGF-β is post-transcriptional (Vodovotz et al. "Mechanisms of suppression of macrophage nitric oxide release by transforming growth factor-β" *J. Exp. Med.*, 1993, vol. 178, pp. 605–614). Only one gene in mouse and man appears to encode iNOS (Chartrain et al., 1994, *J. Biol. Chem., vol.* 269, pp. 6765–6772). The iNOS product is expressible in many and perhaps most nucleated cell types exposed to cytokines and LPS (Nathan C., 1992, *FASEB J.*, vol. 6, pp. 3051–3064). Using monospecific IgG raised against pure iNOS, complementary DNA ("cDNA") was cloned and sequenced (Xie et al., 1992, cited elsewhere herein) by applicants for iNOS. Seventy-eight percent of the deduced amino acid sequence was confirmed by capillary high pressure liquid chromatography ("HPLC") electrospray ionization mass spectroscopy (Xie et al., 1992, cited elsewhere herein).

Although iNOS was cloned from activated macrophages, its cellular distribution includes appropriately stimulated vascular smooth muscle, hepatocytes, fibroblasts, keratinocytes, chondrocytes, epithelial cells, cardiac myocytes, astrocytes, mesangial cells, tumor cells and endothelium. Such widespread distribution may be particularly effective in restricting bacterial and viral infection (Nathan et al., 1991, *Curr. Opin. Immunol.*, vol. 3, pp. 65–70; and Karupiah et al., 1993, *Science, vol.* 261, pp. 1445–1447). Effects of NO produced in the high-output mode include inhibition of proliferation of intracellular pathogens and neighboring host cells, including lymphocytes. These effects are attributable in part to reactivity of NO with the tyrosyl radical in ribonucleotide reductase (Leopivre et al., 1990, *J. Biol. Chem.*, vol. 265, pp. 14143–14149; and Kwon et al., 1991, *J. Exp. Med.*, vol. 174, pp. 761–768) and with Fe—S clusters in three mitochondrial enzymes: cis-aconitase (Hibbs et al., 1990, In "Nitric Oxide from L-Arginine: A Bioregulatory System," S. Moncada and E. A. Higgs, Eds., Elsevier, Amsterdam, pp. 189–223) and electron transport complexes I and II (Stuehr et al., 1989, cited elsewhere herein). Alternatively, systemic or local overproduction of NO by iNOS may in some instances be deleterious, resulting in life-threatening hypotension and multi-organ failure during sepsis or cytokine-induced shock (Kilbourn et al., 1990, *Proc. Natl. Acad. Sci. USA*, vol. 87, pp. 3629–3632; Petros et al., 1991, Lancet, vol. 338, pp. 1557–1558; and Evans et al., 1993, *J. Immunol.*, vol. 150, pp. 5033–5040), or the derangement of individual chronically inflamed organs such as the joints during arthritis (McCartney-Francis et al., 1993, *J. Exp. Med.*, vol. 178, pp. 749–754) or the endocrine pancreas during diabetes (Kleeman et al., 1993, *FEBS Lett.*, vol. 328, pp. 9–12).

3. Induction and Suppression of Inducible Nitric Oxide Synthase

BCG infection of mice endowed their macrophages with the capacity to release nitrite (Stuehr et al., 1985, *Proc. Natl. Acad. Sci. USA*, vol. 82, pp. 7738–7742), as did treatment of macrophages, ex vivo, with IFN-γ+LPS (Stuehr et al., 1987, *J. Immunol.*, vol. 139, pp. 518–525). The NO-inducing potential of a dozen cytokines, alone and in combination with LPS and each other was characterized (Ding et al., 1988, *J. Immunol.*, vol. 141, pp. 2407–2412). The only agents, acting alone, that could induce detectable NO release from mouse macrophages were IFN-γ (Ding et al., 1988, cited elsewhere herein) and LPS (Stuehr et al., 1985, cited elsewhere herein). Maximal NO release always required at least two agents acting in synergy, namely, IFN-γ+LPS, IFN-γ+TNF-α, IFN-γ+TNF-β, IFN-α+LPS, IFN-β+LPS (Ding et al., 1988, cited elsewhere herein). Thus, all the synergistic combinations included an IFN, LPS or a cytokine that LPS can induce. These were later found effective in other cell types (Nathan C., 1992, cited elsewhere herein). Microbes themselves can be effective co-inducers of nitrite release from macrophages, along with IFN-γ, at least in part via the induction and autocrine action of TNF-α (Green et al., 1991, *J. Leuk. Biol.*, vol. 50, pp. 93–103). Just as corticosteroids suppress mouse resistance to Mtb (North et al., 1993, cited elsewhere herein), they also suppress the induction of iNOS (Geller et al., 1993, *Proc Natl. Acad. Sci. USA*, vol. 90, pp. 522–6). iNOS is also suppressed by the cytokines TGF-β (Vodovotz et al., 1990, *J. Immunol.*, vol. 145, pp. 940–944; Barral-Netto et al., 1992, *Science*, vol. 257, pp. 545), IL-4 (Liew et al., 1991, Eur. *J. Immunol.*, vol.

21, pp. 2489) and macrophage deactivation factor (Ding et al., 1990, *J. Immunol.,* vol. 145, pp. 940–944). Thus Mtb infection, like infection with other intracellular parasites of macrophages, could co-induce iNOS (Green et al., 1991, cited elsewhere herein) and/or induce autocrine inhibitors of the induction of iNOS (Barral-Netto et al., 1992, cited elsewhere herein; Bermudez, L. E., 1993, *J. Immunol.*, vol. 150, pp. 1838–45).

4. Human Inducible Nitric Oxide Synthase

Human iNOS complementary deoxyribonucleic acid ("cDNA") has been cloned from activated hepatocytes (Geller et al., 1993, *Proc. Natl. Acad. Sci. USA*, vol. 90, pp. 3491–5) and chondrocytes (Charles et al., 1993, *Proc. Natl. Acad. Sci. USA*, vol. 90, pp. 11419–11423). The enzyme appears to be expressed, in vivo, judging from the massive elevation in plasma and urinary nitrate when human subjects are given Interleukin-2 ("IL-2") (Hibbs et al., 1992, *J. Clin. Invest.*, vol. 89, pp. 867–877) or become septic (Ochoa et al., 1991, *Ann. Surg.*, vol. 214, pp. 621–625).

5. Physiologic Role of Inducible Nitric Oxide Synthase in Resistance to Infection In rodents and/or their macrophages, NO makes a major contribution to macrophage antimicrobial activity against a wide variety of pathogens, including Mtb (Denis, M., 1991, *J. Leuk. Biol.*, vol. 49, pp. 380–387; Flesch et al., 1991, *Infect. Immunol.*, vol. 59, pp. 3213–8; Chan et al., 1992, *J. Exp. Med.*, vol. 175, pp. 111–22; and Doi et al., 1993, *Infect. Immunol.*, vol. 61, pp. 1980–89), M. leprae (Adams et al., 1991, *J. Immunol.*, vol. 147, pp. 1642–1646), leishmania species toxoplasma, cryptococcus (reviewed in Nathan et al., 1991, cited elsewhere herein), herpes simplex virus, ectromelia, and vaccinia virus (Karupiah et al., cited elsewhere herein). The following discussion illustrates this with emphasis on mycobacterial infection.

a. The Tuberculosis Problem: Tuberculosis remains the leading cause of death in the world from a single infectious disease, although there is little knowledge of the mechanisms of its pathogenesis and protection from it. After a century of decline in the United States, tuberculosis is increasing, and strains resistant to multiple antibiotics have emerged (Bloom et al., 1992, *Science*, vol. 257, pp. 1055–64). It is estimated that one-third of the world's population is infected with *Mycobacterium tuberculosis* ("Mtb"), the agent of tuberculosis ("TB"). Furthermore, each year 8 million of those infected with Mtb develop TB, and 2.9 million die of the disease (WHO, 1989, *Bull. Int. Tuberc. Lung Dis.*, vol. 64, pp. 88–111).

Current understanding holds that Mtb resides chiefly within macrophages, and that among the main determinants of its rate of proliferation are: (a) the state of activation of macrophages; (b) the existence of Mtb-specific T cells which respond to Mtb antigens by releasing cytokines that activate macrophages; (c) the existence of non-T cells, mostly natural killer (NK) cells, that also respond to Mtb by releasing macrophage-activating cytokines; (d) the existence of Mtb-specific cytolytic T cells that kill macrophages harboring Mtb; (e) incompletely defined resistance mechanisms based on cells other than those of the lymphohematopoietic system; and (f) products of Mtb that may interfere with, counter or suppress (a)–(e).

b. Resistance To Tuberculosis: The importance of T cells was established by the more rapid proliferation of bacille Calmette Gueérin ("BCG") or Mtb in T cell-deficient nu/nu, $CD4^+$-depleted (Izzo et al., 1992, *J. Exp. Med.*, vol. 176, p. 581, et seq.) or SCID mice (North et al., 1993, *J. Exp. Med.*, vol. 177, pp. 1723–1734) than in wild-type mice. The importance of major histocompatibility complex ("MHC") class I-restricted T cells, presumably chiefly cytolytic T cells, was evident from the relatively rapid proliferation of Mtb in mice rendered deficient in $\beta$2-microglobulin (a component of MHC class I) by homologous recombination (Flynn et al., 1992, *Proc. Natl. Acad. Sci. USA*, vol. 89, pp. 12013–7). However, the same studies, especially when compared to each other, provide cogent evidence for intrinsic resistance involving cells other than cytolytic T lymphocytes ("CTL") in particular or T cells in general. Thus, $\beta$2-microglobulin knock-out mice only sustained the proliferation of virulent Erdmann strain Mtb to a plateau of 6.7 $\log_{10}$ colony forming units ("CFU") per spleen, 6.3 per liver, and 7.3 per lung. This is many orders of magnitude less than in SCID mice: 12.5 in spleen, 10.1 in liver, and 11.8 in lung (North et al., 1993, cited elsewhere herein). These differences presumably reflect either the unanticipated emergence of CTL in such mice (e.g., Apasov et al., 1993, *Proc. Natl. Acad. Sci. USA*, vol. 90, pp. 2837–41) or the contribution of cells other than CTL. When SCID mice were additionally suppressed by the administration of hydrocortisone, Erdmann strain MTB grew to 14.0, 14.0 and 13.2 $\log_{10}$ CFU per spleen, liver and lung, respectively (North et al., 1993, cited elsewhere herein). This further approximately 100-fold increment points to a powerful anti-tuberculous effect of a corticosteroid-sensitive pathway, most likely expressed in macrophages, that is independent of antigen-specific T cells.

c. Antituberculous Role Of Macrophage-Derived Nitric Oxide Mycobacteria can induce NO release from macrophages (Doi et al., 1993, cited elsewhere herein), probably in part via induction of autocrine TNF-$\alpha$ (Green et al., 1991, cited elsewhere herein). With Mtb (Doi et al., 1993, cited elsewhere herein), leishmania (Mauel et al., 1991, *J. Leuk. Biol.*, vol. 49, pp. 73–82), and viruses (Karupiah et al., cited elsewhere herein) a direct microbistatic or microbicidal role for NO was demonstrated through the extracellular addition of No-generating compounds. The role of macrophage-derived NO against intracellular Mtb was studied most thoroughly by Chan et al., 1992, cited elsewhere herein, who demonstrated a close correlation between the production of NO and the ability of IFN-$\gamma$+LPS or IFN-$\gamma$+TNF-$\alpha$ to induce anti-Mtb (Erdmann strain) activity in primary mouse macrophages. Both functions were blocked with $N^\omega$-methyl-L-arginine (L-NMA), a substrate analog inhibitor of iNOS (Chan et al., 1992, cited elsewhere herein). However, autotoxicity from NO can limit the phagocytic and antibacterial functions of macrophages (Doi et al., 1993, cited elsewhere herein). Mycobacterial strains can vary at least 160-fold in their sensitivity to inhibition by chemically generated NO (Doi et al., 1993, cited elsewhere herein). NO resistance has been proposed to play a pathogenic role in mycobacterial strains that induce or co-induce large amounts of NO from macrophages but are not inhibited by it (Doi et al., 1993, cited elsewhere herein).

d. Cytokine-Dependent Mycobacterial Resistance And Induction Of Nitric Oxide Production: Macrophages from wild type mice infected with BCG produce large quantities of NO after stimulation with LPS (Stuehr et al., 1985, cited elsewhere herein). In contrast, macrophages from IFN-$\gamma$-"knock-out" (gko) mice infected with BCG produced little detectable NO after stimulation with LPS. The defect was reversed when the gko cells were treated with IFN-$\gamma$ for 48 hours in vitro (Dalton et al., 1993, *Science*, vol. 259, pp. 1739–42). BCG grew faster in the gko mice than in the wild type. Thus, IFN-$\gamma$ appears to be necessary to prime macrophages for the production of NO in response to BCG, and NO may be important in mycobacterial growth inhibition or killing. The production of reactive oxygen intermediates was also reduced in gko macrophages from BCG-infected mice. Because of the pleiotropic nature of IFN-γ, it is not possible to determine whether the enhanced survival of BCG in gko mice reflects the relative importance of the reduction in NO, the reduction in oxidative burst, defects in T cell activation, or other consequences of IFN-γ deficiency. In human macrophages in vitro, IFN-γ only weakly impairs Mtb proliferation (Douvas et al., 1985, *Infect. Immunol.*, vol. 50, pp. 1–8), suggesting that other cytokines may be more important, and/or that conditions used with human macrophages in vitro are inimical to their activation by IFN-γ. IFN-γ, used alone, does not activate human macrophages in vitro for NO release. However, the administration of human recombinant IFN-γ to 6 patients with drug-resistant atypical mycobacteriosis led to dramatic improvement in all 6 patients (Holland et al., 1994, New Engl. *J. Med.*, vol. 330, pp. 1348–1355). This important observation may suggest that IFN-γ is a more effective antimycobacterial agent in vivo than in vitro, perhaps reflecting positive interaction with other cytokines. Thus, existing evidence in both human and mouse supports the hypothesis that there may be a close correlation between activation for nitric oxide release and inhibition of Mtb replication.

e. Inducibility And Function Of iNOS In Epithelial Cells: Although most Mtb are found within macrophages during Tb infection, this does not necessarily exclude a role for secretory products derived from other cells, such as respiratory epithelium. This is particularly relevant with respect to NO, for the following reasons: (1) NO generated by transfected iNOS in one epithelial cell can exert an antiviral effect within neighboring cells (Karupiah et al., 1993, cited elsewhere herein); (2) Cytokine-treated epithelial cells can produce high levels of NO, as described for murine and human keratinocytes, and can respond to it with diminished proliferation (Heck et al., 1992, *J. Biol. Chem.*, vol. 267, pp. 21277–80); (3) Respiratory epithelium in particular can be induced by cytokines and microbial products not only to produce NO but also to respond to it with decreased ciliary function or destruction of the epithelial lining (Heiss et al., 1994, Proc. Natl. Acad. Sci., USA, vol. 91, pp. 267–270); (4) Applicants' anti-iNOS antibody stains abundant iNOS protein throughout the entire alveolar epithelial surface in mice subjected to ozone intoxication (Pendino et al., 1993, J. Immunol., vol. 151, pp. 7196–7205).

f. Role Of Nitric Oxide In The Lung: NO regulates bronchial tone, pulmonary vascular resistance, and ventilation-perfusion matching, in addition to systemic blood pressure (Nathan C., 1992, cited elsewhere herein), the beating rate of cardiac myocytes (Roberts et al., 1992, Molec. Endocrinol., vol. 6, pp. 1921–30), and cardiac contractility (Finkel et al., 1992, *Science*, vol. 257, pp. 387–389). Inhibition of NO production by administration of L-NMA improves the course of hepatic listeriosis, apparently because the predominant action of NO in this setting is inhibition of T cell proliferation rather than a direct antimicrobial action (Gregory et al., 1993, *J. Immunol.*, vol. 150, pp. 2901–9). This could be the case with other infections in other organs, including the lung. Thus, the diverse roles of NO in immunology and pulmonary physiology (Nathan, C., 1992, cited elsewhere herein) make it difficult to interpret results of experiments in which all isoforms of NO are inhibited pharmacologically in all cell types. In particular, the apparent importance of oxygenation in affecting the grown of Mtb in the lung (Gregory et al., 1993, cited elsewhere herein) makes it desirable not to interfere with constitutive NOS in blood vessels and neurons when investigating the role of iNOS in macrophages and respiratory epithelium.

g. Host Resistance to *Mycobacterium tuberculosis:* Our ability to improve host resistance to Mtb is encumbered by our lack of understanding of the biochemical basis of the restriction of Mtb replication by activated macrophages, lack of experimental approaches to the evaluation of an antituberculous contribution by the respiratory epithelium, and ignorance of the genetic and biochemical bases of mycobacterial resistance to host anti-tuberculous defenses. Mycobacterial resistance to host defense is likely to be multifactorial and might include evasion from triggering NK cells, suppression of the action of IFN-γ, suppression of induction or action of host defense enzymes in response to IFN-γ, and resistance to the antimicrobial products of such enzymes. A better understanding of each of these points might lead to the design of improved anti-tuberculosis therapy, either pharmacologic or immunologic.

h. Role Of Nitric Oxide In Controlling Tuberculosis: Evidence that NO could play a role in the control of TB can be summarized as follows: (1) Macrophages from mice infected with BCG (Stuehr et al., 1987, cited elsewhere herein) and cytokine-treated, mycobacteria-infected human macrophages produce NO (Denis, M., 1991, cited elsewhere herein); (2) mycobacteria can induce NO production from rat macrophages infected in vitro (Doi et al., 1993, cited elsewhere herein); (3) mouse and rat macrophages use NO to kill Mtb in vitro (Denis, M., 1991, cited elsewhere herein; Flesch et al., 1991, cited elsewhere herein; Chan et al., 1992, cited elsewhere herein; and Doi et al., 1993, cited elsewhere herein); (4) macrophages from mice incapable of making (Apasov et al., 1993, cited elsewhere herein) or responding to IFN-γ (Huang et al., 1993, *Science*, vol. 259, pp. 1742–45) are deficient in producing NO; (5) BCG grows more rapidly in such mice (Apasov et al., 1993, cited elsewhere herein); (6) the macrophage-specific product of the Bcg gene is predicted to encode a nitrite transporter (Vidal et al., 1993, cited elsewhere herein). Although this evidence is no more than suggestive, it warrants testing this hypothesis. However, it would be difficult to do so by the simple expedient of using NOS inhibitors in vivo. The diverse roles of No in immunology and pulmonary physiology make it difficult to interpret results of experiments in which all isoforms of No are inhibited pharmacologically in all cell types. Unfortunately, iNOS-specific inhibitors are not available. Likewise, existing knock-out mice fall short of defining the role of NO in host defense against Mtb. In particular, the pleiotropic nature of IFN-γ makes it impossible to determine whether the enhanced survival of BCG in IFN-γ knock-out mice results from the reduction in NO, the decreased oxidative burst, defects in T cell responses, or other consequences of IFN-γ deficiency. As a potential animal model for rapid growth of Mtb, β2-microglobulin knock-out mice are suboptimal in that they appear to show substantial residual resistance to Mtb. Genetic approaches that knock out iNOS selectively should provide an unambiguous answer to the importance of iNOS in defense of the host against Mtb, and at the same time may generate mice whose immune system and overall physiology have undergone the least perturbation consistent with allowing Mtb to replicate rapidly.

6. Pathophysiologic Role of Inducible Nitric Oxide Synthase in Inflammatory Disorders Indirect evidence suggests that the action of inducible nitric oxide synthase may be essential for the development of various forms of inflammatory tissue damage, examples of which are provided below. If this could be confirmed or refuted by compelling evidence, it would help investigators decide whether or not to direct their efforts and resources to the development of pharmacologic agents that serve as inducible nitric oxide synthase-specific inhibitors. Mice genetically deficient in inducible nitric oxide synthase would provide an avenue toward obtaining such compelling evidence. In contrast, the existing evidence implicating inducible nitric oxide synthase is not conclusive because in each case it is based on the following two points, each with a major limitation as indicated:

(a) The disorder is expressed under conditions in which inducible nitric oxide synthase is induced. Limitation: The same conditions may lead to enhanced activity of other nitric oxide synthase by indirect routes, or the disorder may critically depend on basal activity of other nitric oxide synthase. For example, bacterial lipopolysaccharide (LPS), which induces inducible nitric oxide synthase in vitro (Stuehr et al., 1987, cited herein; Ding et al., 1988, cited herein) and in vivo (Lowenstein et al., 1992, *Proc.Natl.Acad.Sci. USA*, vol. 89, pp. 6711–6715), also induces interferon-gamma (IFN-γ) (Billiau, A. and Matthys, P., 1992, Cytokine, vol. 4, pp. 259–263). LPS can interact with IFN-γ to induce enzymes that increase the level of tetrahydrobiopterin (Gross et al., 1992, *J. Biol. Chem.*, vol. 267, pp. 25722–25729), a cofactor of all nitric oxide synthase (Nathan, 1992, cited herein). Moreover, LPS can interact with IFN-γ to induce enzymes that increase the level of the con-version of L-citrulline (Hattori et al., 1994, *J. Biol. Chem.*, vol. 269, pp. 9405–9408), the product of all nitric oxide synthase (Nathan, 1992, cited herein), to L-arginine, a substrate of all nitric oxide synthase (Nathan, 1992, cited herein). In such ways, LPS and IFN-γ can markedly enhance the amount of nitric oxide made by the constitutive nitric oxide synthase of endothelial cells even though the amount of this constitutive endothelial nitric oxide synthase does not increase (Rosenkranz-Weiss et al., 1994, *J. Clin. Invest.*, vol. 93, pp. 2236–2243). Further, the central and peripheral nervous systems can be involved in regulation of vascular permeability and blood pressure. It is thus possible that constitutive neural nitric oxide synthase may play a role in local and systemic inflammatory responses, even when the latter are elicited by stimuli that induce inducible nitric oxide synthase. For these reasons, it is not possible to conclude from the nature of the inciting stimuli which nitric oxide synthase actually contribute critically to the disorder under study.

(b) Compounds that inhibit inducible nitric oxide synthase, prevent or ameliorate the disorder. Limitation: Such compounds inhibit all known nitric oxide synthase, including but not limited to inducible nitric oxide synthase (Nathan, 1992, cited herein), and their inhibition is rarely complete. As with any drug, such compounds may have additional effects unrelated to their intended target. Thus, it is unknown whether the inhibition of inducible nitric oxide synthase by such compounds is complete, whether the inhibition of inducible nitric oxide synthase rather than another nitric oxide synthase is the relevant action, or whether the anti-inflammatory effect results in whole or in part from an additional action of the compounds unrelated to inhibition of any nitric oxide synthase.

Therefore, it would be of great utility to the enterprise of drug development to provide a strain of mice in which a deficiency of inducible nitric oxide synthase is (a) selective, (b) genetically rather than pharmacologically induced, and (c) complete. It could then be determined whether this selective, complete, drug-free deficiency of inducible nitric oxide synthase diminishes the expression of certain experimental inflammatory diseases in mice. This could be determined by treating inducible nitric oxide synthase-deficient and wild-type mice with the agents that normally induce inflammatory tissue damage and comparing the outcomes in the two strains of mice. Additionally or alternatively, this could be determined by interbreeding inducible nitric oxide synthase-deficient mice with mice of strains that are genetically prone to the spontaneous or experimentally induced development of inflammatory tissue damage and comparing the resulting strains of mice with the parental strains for the incidence and severity of disease.

Information from the literature, summarized below, supports the reasoning advanced above:

(a) Arthritis, glomerulonephritis, pneumonitis, carditis, enteritis: Arthritis can be induced in rats by the intraperitoneal injection of streptococcal peptidoglycans (McCartney-Francis et al., 1993, cited herein). The arthritis is accompanied by expression of inducible nitric oxide synthase mRNA and the production of nitrite, an inducible nitric oxide synthase product, in the joint tissue (McCartney-Francis et al., 1993, cited herein). Administration of N-monomethyl-L-arginine (NMA), an inhibitor of nitric oxide synthase, prevents the development of the arthritis (McCartney-Francis et al., 1993, cited herein). Similar results have been described for adjuvant-induced arthritis in rats (Ialenti et al., 1993, Br. *J. Pharmacol.*, vol. 1 10, pp. 701–706); mice strains are also susceptible to induced arthritis, e.g., collagen induced arthritis (Courtenay et al., 1980, Nature vol. 285, pp. 666–668; Wooley et al., 1985, *J. Immunol.* vol. 135, pp. 2443–2451). Moreover, arthritis and glomerulonephritis appear spontaneously in MRL-l pr/l pr strain mice during the course of a disease that is considered a model for the human disease, systemic lupus erythematosus (Weinberg et al., 1994, *J. Exp. Med.*, vol. 179, pp. 651–660), and NMA meliorates this disease in MRL-l pr/l pr mice. In humans with rheumatoid arthritis, synovial fluid from inflamed joints contains high levels of nitrate (Farrell et al., 1992, *Ann. Rheum. Dis.*, vol. 51, pp. 1219–1222), which can be a product of inducible nitric oxide synthase, and inducible nitric oxide synthase cDNA has been cloned from cytokine-treated human articular chondrocytes (Charles et al., 1994, *Proc. Natl. Acad. Sci. USA*, vol. 90, pp. 11419–11423). In mice rendered genetically deficient in transforming growth factor-β1 (TGFβ1), the heart, pancreas, lung, intestinal tract and other organs become infiltrated with mononuclear leukocytes and the animals die at 3–4 weeks of age (Kulkarni et al., 1993, *Proc. Natl. Acad. Sci. USA*, vol. 90, pp. 770–774). Because TGF-β1 is an inhibitor of inducible nitric oxide synthase expression (Vodovotz et al., 1993, cited herein) and because serum nitrate is markedly elevated in these mice before death (personal communication, Y. Vodovotz), the lethal inflammatory disorder in these mice may reflect the failure of a normal restraint on inducible nitric oxide synthase expression. Inducible nitric oxide synthase is induced by LPS and by irritant chemicals in the small intestine and colon of the rat in association with increased intestinal vascular permeability (Houghton-Smith et al., 1993, *Agents Actions*, vol. 38, pp. C125–126), and inducible nitric oxide synthase activity is elevated in the colonic mucosa from patients with ulcerative colitis (Boughton-Smith et al., 1993, *Lancet*, vol. 342, pp. 338–340). Immune complex induced vasculitis in the skin and lung of rats was blocked by inhibitors of nitric oxide synthase (MuWgan et al., 1992, *Proc. Natl. Acad. Sci. USA*, vol. 107, pp. 1159–1162).

(b) Septic shock: The most frequent cause of death in intensive care units in the United States today (about 100,000 deaths per year) is thought to be septic shock (Natanson et al., 1994, *Ann. Int. Med.*, vol. 120, pp. 771–783). In septic shock, overwhelming infection causes the blood pressure to fall too low to keep organs functioning normally. These effects of septic shock can be reproduced by injection of bacterial lipopolysaccharide, or LPS. Large amounts of endogenously derived nitric oxide are produced during septic shock and can make blood vessels dilate so that blood pressure falls and no longer responds to adrenalin or any other standard treatment. LPS induces inducible nitric oxide synthase in vitro (Stuehr et al., 1987, cited herein; Ding et al., 1988, cited herein) and in vivo (Lowenstein et al., 1992, *Proc. Natl. Acad. Sci. USA*, vol. 89, pp. 6711–6715). In dogs (Kilbourn et al., 1990, cited herein) experiencing shock following injection of LPS, and in human patients experiencing clinical septic shock (Petros et al., 1991, cited herein), compounds that block nitric oxide synthase have protected the blood pressure from falling.

(c) Insulitis and insulin-dependent diabetes mellitus (IDDM): Several strains of mice and rats are prone to spontaneous development of inflammation in the pancreatic islets of Langerhans, leading to destruction of insulin-producing β cells and consequent insulin insufficiency, resulting in IDDM. In such animals, production of inducible nitric oxide synthase in the islets has been demonstrated before the onset of symptomatic disease (Kleeman et al., 1993, cited herein). IDDM can also be induced by the nitric oxide-generating toxin, streptozotocin (Kwon et al., 1994, *FASEB J.*, vol. 8, pp. 529–533), and by nitric oxide-inducing cytokines (Southern et al., *FEBS Lett.* vol. 276, pp. 42–44; Welsh et al., *Endocrinology*, vol. 129, pp. 3167–3173; Corbett et al., *J. Biol. Chem.*, vol. 266, pp. 21351–21354; Kolb, H. and Kolb-Bachofen, V., 1992, *Diabetologia*, vol. 35, pp. 796–797; Corbett et al., 1992, *Diabetes*, vol. 41, pp. 897–903). In these situations, islet cell destruction can be prevented by compounds that inhibit inducible nitric oxide synthase (Southern et al., *FEBS Lett.*, vol. 276, pp. 42–44; Welsh et al., *Endocrinology*, vol. 129, pp. 3167–3173; Corbett et al., *J. Biol. Chem.*, vol. 266, pp. 21351–21354; Kolb, H. and Kolb-Bachofen, V., 1992, *Diabetologia*, vol. 35, pp. 796–797; Corbett et al., 1992, *Diabetes*, vol. 41, pp. 897–903).

d. *Encephalitis, meningitis*, encephalomyelitis: Inflammation within the central (CNS) and peripheral nervous systems often arises as a consequence of viral or bacterial infections, or may involve predisposing genetic factors in the case of autoimmune disorders such as multiple sclerosis (MS). Regardless of origin, inducible nitric oxide synthase has been associated with several of these processes. In mice with rabies, lymphocytic choriomeningitis or herpes simplex viral infections, cerebral expression of iNOS closely correlates with the incidence and severity of disease (Koprowski et al., 1993, *Proc. Natl Acad. Sci. USA.*, vol. 90, pp. 3024–3027; Campbell et al., 1994, submitted). Release of NO by inflammatory cells entering the CNS lesions of mice and rats with experimental autoimmune encephalomyelitis, a model for human MS, is also thought to contribute to the edema and motor dysfunction characteristic of this disorder (MacMicking et al., 1992, *J. Exp. Med.*, vol 176, pp. 303–307; Koprowski et al., 1993, cited elsewhere herein; Lin et al., *J. Exp. Med.*, vol. 178, pp. 643–648). Moreover, the NOS inhibitor aminoguanidine, ameliorated the course of experimental autoimmune encephalomyelitis in mice (Cross et al., 1994, *J. Clin. Invest.*, vol. 93, pp. 2684–2690). NO may emanate from sources other than perivascular inflammatory cells, notably resident microglia, which have the ability to secrete large amounts of NO and kill neighboring oligodendrocytes following cytokine stimulation (Galea et al., 1992, *Proc. Natl Acad. Sci. USA.*, vol. 89, pp. 10945–10949; Merril et al., 1993, *J. Immunol.*, vol. 151, pp. 2132–2141). Clearly, the alternate cellular sources of NO, its elicitation by multiple stimuli and the reduced antioxidant status of the CNS (Honeggar et al., 1989, *Neurosci. Lett.*, vol 98, pp. 327–333) strongly support a neuropathogenic role for iNOS.

7. Need for a Mouse Strain Expressing a Targeted Disruption of the Gene Encoding Inducible Nitric Oxide Synthase A description of the precise physiological functions performed by members of the NOS gene family, to date, has been based on investigating biologic events within monotypic cell cultures, isolated in situ tissue preparations and whole animal models. In many cases, attributing effects to the product of any single NOS gene has been hampered by differing responses to stimuli depending on cellular locale and overlapping patterns of tissue expression. Most importantly, it has not been possible to inhibit completely or with absolute specificity any one isoform of NOS in whole animal studies using the currently available pharmacologic inhibitors. Targeted gene disruption has arisen as a powerful experimental approach now used to better delineate the roles played by various members of multigene families (Koller et al., 1992, *Ann. Rev. Immunol.*, vol. 10, pp. 705–730). Thus far only the neural isoform of cNOS has been reported as disrupted via gene targeting methods (Huang et al., 1993, *Cell*, vol. 75, pp. 1273–1286). Phenotypically such mice appear grossly normal except for gastric hypertrophy, survive until adulthood and are fertile. Effective disruption of the neural cNOS locus is manifested by an immunohistological absence of this isoform in both the central and peripheral nervous systems, coupled with partial loss of enzymatic activity. The functional status of the intact iNOS and endothelial cNOS loci in these mice has not been described.

Transgenic mice exhibiting a partially dysfunctional iNOS phenotype have been created via targeting of either the interferon-gamma (IFN-γ) gene (Dalton et al., 1993, *Science*, vol. 259, pp. 1739–1742), of the gene encoding the ligand-binding chain of its receptor (IFN-γR) (Huang et al., 1993, *Science*, vol. 259, pp. 1739–1745) or of the gene encoding interferon regulatory factor-1 (Kimijo et al., 1994, *Science*, vol. 263, pp. 1612–1615), a transcription factor involved in induction of iNOS.

Impaired anti-mycobacterial properties are seen with all three of the IFN-γ-related gene targeted mice that have secondary insufficiency of iNOS expression, namely those with disrupted genes for IFN-γ Dalton et al., cited elsewhere herein), the IFN-γ receptor (Huang et al., cited elsewhere herein), or interferon-regulatory factor 1 (Kimijo et al., cited elsewhere herein). Increased resistance to an otherwise lethal dose of bacterial lipopolysaccharide (LPS) is observed in at last one of these strains, namely, that with a disrupted gene for the IFN-γ receptor (Kimijo et al., 1993, *J. Exp. Med.*, vol. 178, pp. 1435–1440). The iNOS defect can be partially restored in IFN-γ-deficient animals by systemic administration of exogenous IFN-γ, and in IFN-γ R-deficient mice by treatment with alternate stimuli (i.e., IFNs-α or β plus LPS) (Huang et al., *Science*, 1993, cited elsewhere herein). Aside from the above examples of a diminished, although not congenitally absent, iNOS activity in gene-targeted animals, there appear to be no reports of an inducible nitric oxide synthase-deficient transgenic mouse. Therefore, a need exists for the development of an otherwise healthy, inexpensive, inducible nitric oxide synthase-deficient transgenic strain of mouse. Such a strain could be used for supporting the rapid replication of Mtb and other microbial or viral pathogens in order to best test for antiinfectious agents. Such a strain could also be used for definitive tests of the role of inducible nitric oxide synthase in inflammatory tissue damage in such settings as arthritis, glomerulonephritis, pneumonitis, carditis, enteritis, septic shock, insulin-dependent diabetes mellitus, and encephalomyelitis.

SUMMARY OF THE INVENTION

It is, therefore, the primary object of the present invention to provide an inducible nitric oxide synthase ("iNOS")-deficient transgenic mouse.

The present invention provides an inducible nitric oxide synthase ("iNOS")-deficient transgenic mouse, also termed an "iNOS Knock-Out mouse". The somatic and germ cells of the transgenic mouse (mice) contain a gene coding for a disrupted inducible nitric oxide synthase ("iNOS") protein. The disruption occurs at a level sufficient to interfere with production of iNOS and/or alter the protein and/or interfere with production of nitric oxide by the protein. The disrupted iNOS gene was introduced into the mouse, or an ancestor thereof, at an embryonic stage using any known technique in the art, such as microinjection or co-culturing ES cells with blastocysts. The deficient transgenic mouse (mice) of the invention exhibit a phenotype characterized by the substantial absence of nitric oxide-producing iNOS. This phenotype is conferred to the mouse by the disruption of the mouse iNOS gene in the somatic and germ cells of the mouse. This disruption introduces a chromosomal defect into the mouse iNOS gene at a sequence of the iNOS gene functionally important for production of wild type iNOS protein and/or the protein's production of NO, thereby preventing the endogenous gene from producing wild type iNOS and/or NO in the mouse.

In another embodiment of the invention, there is provided a vector(s) designed for the disruption of the mouse iNOS gene. The vector, designated piNOS-RV1, disrupts i.e., introduces a genetic defect, in the iNOS locus of the murine chromosome. Embryonic stem cell(s) having a disrupted iNOS allele following transfection with this vector are identified for generating iNOS-deficient transgenic mice. A host cell line or cell clone carrying a congenitally altered iNOS gene are provided.

A method of producing a heterozygous mouse whose somatic and germ cells contain a gene coding for a disrupted inducible nitric oxide synthase is also disclosed. The method comprises (a) providing a gene coding for a disrupted inducible nitric oxide synthase, the disruption having occurred at a level sufficient to prevent expression of inducible nitric oxide synthase and/or production of nitric oxide by inducible nitric oxide synthase; (b) introducing the gene into a blastocyst; (c) transplanting said embryo into a pseudopregnant mouse and allowing the blastocyst to develop to term; (d) identifying a mouse which carries the deficiency in one allele, (e) identifying a mouse which carries the deficiency in both alleles, the mouse exhibiting a phenotype characterized by the substantial absence of expression of inducible nitric oxide synthase and/or production of nitric oxide by inducible nitric oxide synthase.

A method is also disclosed for producing a homozygous transgenic mouse in accordance with the invention.

The transgenic mouse (mice) produced in accordance with the invention can be evaluated for their susceptibility to infectious or tumorigenic challenge, autoimmunity, pharmacological and/or chemical agents and bacterial sepsis. For example, the transgenic mouse (mice) can be used as a model in which *Mycobacterium tuberculosis* can replicate efficiently and quickly to search for new anti-tuberculosis therapies. The transgenic mouse (mice) of the invention, aside from susceptibility to acquire certain infections, such as *Mycobacterium tuberculosis*, are otherwise healthy animals as well as relatively inexpensive to produce.

The mice can also be bred onto appropriate murine genetic backgrounds to enable changes in disease susceptibility to be examined. Examples are LPS-induced shock (129 mice), experimental collagen induced arthritis (e.g., B10.RIII and DBA-1 mice), spontaneous insulin dependent diabetes (NOD mice), multiple spontaneous autoimmune disease (MRL-1pr/1pr mice), and experimental autoimmune encephalomyelitis (EAE).

BRIEF DESCRIPTION OF DRAWINGS

FIG. 3 shows the orientation of the murine iNOS gene [(a) Overlapping cosmid clones which comprise the murine iNOS contig. (b) Detailed map of the 5' end of the iNOS gene. Letter codes=A, ApaI; b, BamHI; E, EcoRI; H, HindIII; Hn, HincII; K, KpnI; p, PstI; and Xb, XbaI. Only the HincII sites used to subclone the 5'promoter region are shown. Exons 1–8 of mouse iNOS, corresponding to about 1000 base pairs (bp) of iNOS coding sequence, are shown as black boxes. The location of exon 6 is approximate].

DETAILED DESCRIPTION OF THE INVENTION

Figure 1:
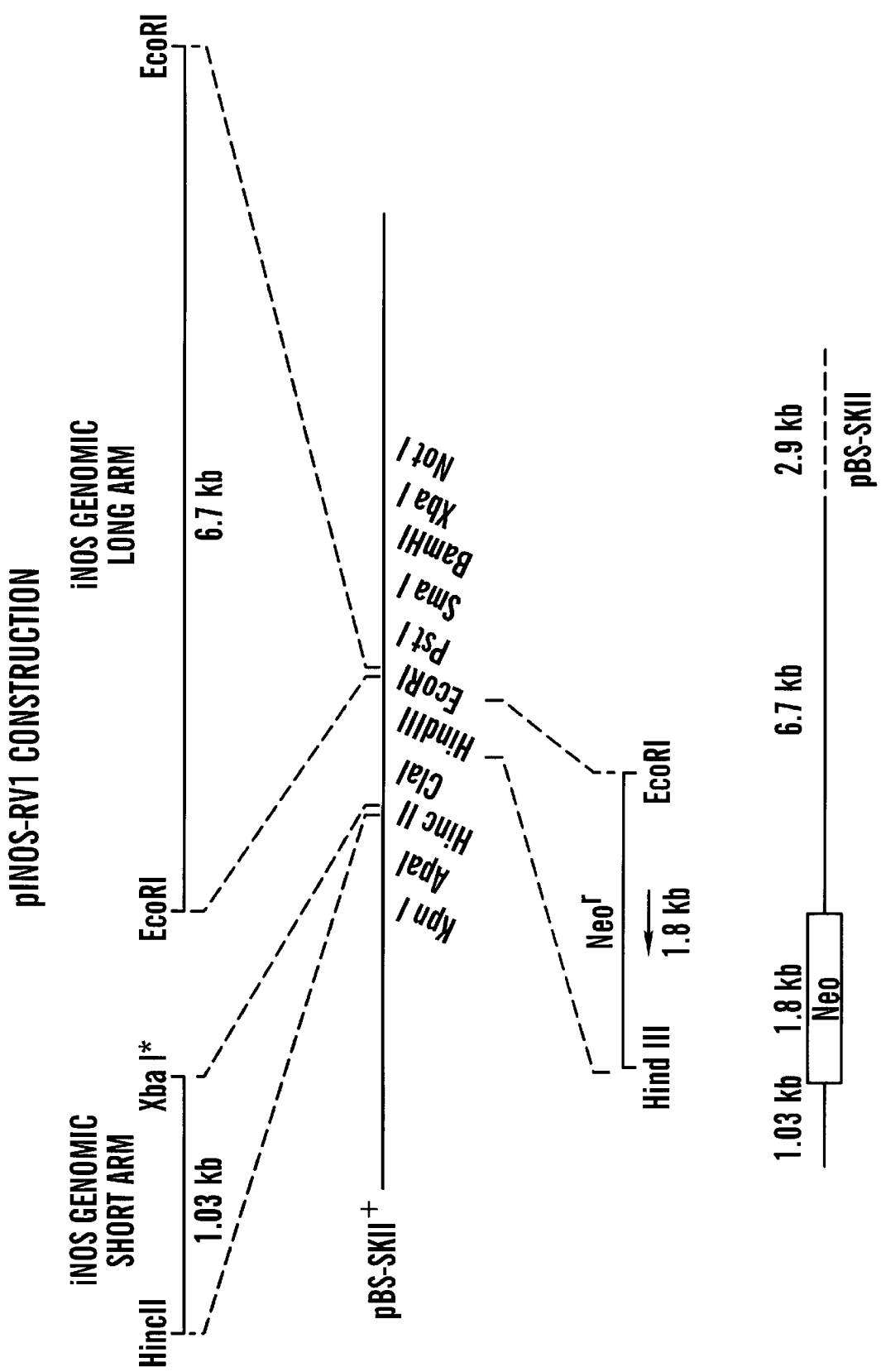
FIG. 1 shows a restriction map of the replacement vector designated piNOS-RV1. The asterisk denotes the baI site region lost by spontaneous sequence deletion.

As used throughout this specification, the following definitions apply for purposes of the present invention:

The term "vector" refers to an extra-chromosomal molecule of duplex DNA comprising an intact replicon that can be replicated in a cell. Generally, vectors are derived from viruses or plasmids of bacteria and yeasts.

The term "gene" refers to those DNA sequences which transmit the information for and direct the synthesis of a single protein chain. The "iNOS gene" refers to any gene comprising a DNA sequence which encodes for inducible nitric oxide synthase.

The term "plasmid" means a virus-derived vector capable of infecting bacteria which is used as an intermediate. A plasmid facilitates the transfer of exogenous genetic information, such as the combination of a novel promoter and a heterologous structural gene under the regulatory control of that promoter, to a specific site within a genome by homologous recombination via the DNA sequences flanking the chimeric gene. The plasmid can itself express a heterologous gene inserted therein.

"Plasmids" are designated by a lower case p preceded and/or followed by capital letters and/or numbers. The starting plasmids herein are commercially available, are publicly available on an unrestricted basis, or can be constructed form such available plasmids in accord with published procedures. In addition, other equivalent plasmids are known in the art and will be apparent to one of ordinary skill in the art.

The term "replacement vector," as used herein, refers to a plasmid vector containing genomic DNA homologous to the endogenous mouse iNOS gene loci and at least one gene coding for a selectable marker.

The term "transfection" or "transfected," as used herein, refers to any means for introducing the vector into a cell. Examples of such means include infection, transformation, calcium phosphate precipitation and electroporation.

The terms "mutation" and "disruption" as used herein, are analogous and refer to any alteration in the genetic code i.e., nucleic acid sequence. With reference to the "iNOS gene", the terms "mutation" and "disruption" refer to the altering and/or disrupting of nucleic acid sequence(s) coding for the iNOS gene or other functionally important sequences (e.g., promoter region, polyadenylation region) of the iNOS gene by the replacement vector (e.g., nucleic acid sequence from vector disrupts iNOS gene sequence upon homologous recombination between the vector and iNOS gene). This alteration and/or disruption can include, without limitation, insertion of the vector nucleic acid into the iNOS loci within a coding exon(s), between exons, and in so doing remove the intervening coding sequence, and/or into other functionally important sequences such that loss of function of the iNOS gene ensues e.g., substantial absence of expression of inducible nitric oxide synthase and/or production of nitric oxide by inducible nitric oxide synthase.

The term "restriction enzyme digestion" of DNA refers to catalytic cleavage of the DNA with an enzyme that acts only at certain locations in the DNA. Such enzymes are called restriction endonucleases, and the site for which each is specific is called a restriction site. The various restriction enzymes used herein are commercially available and their reaction conditions, cofactors, and other requirements as established by the enzyme suppliers are used. Restriction enzymes commonly are designated by abbreviations composed of a capital letter followed by other letters representing the microorganism from which each restriction enzyme originally was obtained and then a number designating the particular enzyme. In general, about 1 $\mu$g of plasmid or DNA fragment is used with 1–2 units of enzyme in about 20 $\mu$l of buffer solution. Appropriate buffers and substrate amounts for particular restriction enzymes are specified by the manufacturer. Incubation of about 1 hour at 37° C. is ordinarily used, but may vary in accordance with the supplier's instructions. After incubation, protein or polypeptide is removed by extraction with phenol and chloroform, and the digested nucleic acid is recovered from the aqueous fraction by precipitation with ethanol. Digestion with a restriction enzyme may be followed with bacterial alkaline phosphatase hydrolysis of the terminal 5' phosphates to prevent the two restriction cleaved ends of a DNA fragment from circularizing or forming a closed loop that would impede insertion of another DNA fragment at the restriction site. Unless otherwise stated, digestion of plasmids is not followed by 5' terminal dephosphorylation. Procedures and reagents for dephosphorylation are conventional as described in Sections 1. 56–1.61 of Sambrook et al., *Molecular Cloning: A Laboratory Manual* New York: Cold Spring Harbor Laboratory Press, 1989, which disclosure is hereby incorporated by reference).

The term "Southern blot analysis" is a method by which the presence of DNA sequences in a restriction endonuclease digest of DNA or DNA-containing composition is confirmed by hybridization to a known, labeled oligonucleotide or DNA fragment. Southern analysis typically comprises electrophoretic separation of DNA digests on agarose gels, denaturation of the DNA after electrophoretic separation, and transfer of the DNA to nitrocellulose, nylon, or another suitable membrane supports for analysis with a radiolabeled, biotinylated or enzyme-labeled probe as described in sections 9.37–9.52 of Sambrook et al., supra, which disclosure is hereby incorporated by reference.

The term "ligation" means the process of forming phosphodiester bonds between two nucleic acid fragments. To ligate the DNA fragments together, the ends of the DNA fragments must be compatible with each other. In some cases, the ends will be directly compatible after endonuclease digestion to blunt ends to make them compatible for ligation. To blunt the ends, the DNA is treated in a suitable buffer for at least 15 minutes at 15° C., with about 10 units of the Klenow fragment of DNA polymerase I or T4 DNA polymerase in the presence of the four deoxyribonucleotide triphosphates. The DNA is then purified by phenolchloroform extraction and ethanol precipitation. The DNA fragments that are to be ligated together are put in solution in about equimolar amounts. The solution will also contain ATP, ligase buffer, and a ligase such as T4 DNA ligase at about 10 units per 0.5 $\mu$g of DNA. If the DNA is to be ligated into a vector, the vector is first linearized by digestion with the appropriate restriction endonuclease(s). The linearized fragment is then treated with bacterial alkaline phosphatase, or calf intestinal phosphatase to prevent self-ligation during the ligation step.

The present invention provides an inducible nitric oxide synthase ("iNOS")-deficient transgenic mouse, also termed "iNOS Knock-Out mouse". The transgenic mouse (mice) somatic and germ cells contain a gene coding for a disrupted inducible nitric oxide synthase ("iNOS") protein. The transgenic mouse (mice) of the invention exhibit a phenotype characterized by the substantial absence of nitric oxide producing inducible nitric oxide synthase. This phenotype is conferred to the mouse by the disruption of the mouse iNOS gene in the somatic and germ cells of the mouse. The disruption occurs at a level sufficient to prevent expression of iNOS and/or production of nitric oxide by inducible nitric oxide synthase. This disruption i.e. mutation, introduces a chromosomal defect into the mouse iNOS gene, thereby preventing the endogenous gene from producing iNOS and/or nitric oxide in the mouse. The disrupted iNOS gene was introduced into the mouse, or an ancestor thereof, at an embryonic stage using any known technique in the art, such as microinjection or co-culturing ES cells with blastocysts.

In accordance with the invention, the mouse iNOS gene is disrupted i.e., chromosomal defect introduced into the iNOS gene loci, using a vector. Preferably, the vector is a replacement vector, although disruption of the iNOS gene can be accomplished using any known vector in the art. Examples of such vectors include, without limitation, (1) an insertion vector(s) as described by Capecchi, M. R., 1989, *Science*, vol. 244, pp. 1244–1292, which disclosure is hereby incorporated by reference; and (2) vector(s) based on promoter trap, polyadenylation trap, "hit and run" or "tag-and-exchange" strategies, as described by Bradley et al., 1992, *Biotechnology*, vol. 10, pp. 534–539; and Askew et al., 1993, *Mol. Cell Biol.*, vol. 13, pp. 4115–4124, which disclosures are hereby incorporated by reference. These vectors may or may not include negative selection markers (e.g., the HSV-tk and DT-A genes), which when used, may allow enhancement of targeted recombinant isolation (Mansour et al., 1988, *Nature*, vol.336, pp. 348–352; McCarrick et al., 1993, Transgen. Res., vol. 2, pp. 183–190). These markers may be part of the targeting vector, or may be co-transfected into the ES cells.

The vector(s) of the invention can be prepared using standard genetic engineering technologies known to the art, such as described by Maniatis et al., 1982, *Molecular Cloning: A Laboratory Manual*, Cold Spring Laboratory, Cold Springs Harbor, N.Y.; and Sambrook et al., (*Molecular Cloning: A Laboratory Manual* New York: Cold Spring Harbor Laboratory Press, 1989, which disclosures are hereby incorporated by reference.

The preferred replacement vector of the invention is designated piNOS-RV1 (FIG. 1). It is understood that DNA fragments and a large number of vectors known in the art can be used herein, such as, for example, plasmids, bacteriophage virus or other modified viruses, provided the vectors can incorporate the nucleic acid construct for disruption of the iNOS gene. Examples of suitable vectors include viral vectors such as lambda vector system gt11, gtWES.tB, Charon 4 and plasmid vectors such as pBR322, pBR325, pACYC177, pACYC184, pAR series, pKK223-3, pUC8, pUC9, pUC18, pUC19, pLG339, pR290, pKC37, pKC101 and other similar systems.

The iNOS gene was characterized in sufficient detail to permit the design of the replacement vector(s) of the invention so that upon homologous recombination between the replacement vector and the endogenous mouse iNOS gene, the natural mouse gene is disrupted sufficiently to prevent the gene from expressing inducible nitric oxide synthase and/or production of nitric oxide by the protein.

More particularly, the 5'-UTR of the iNOS gene (i.e., 1749 base pairs) was cloned and sequenced from a mouse embryonal stem cell genomic library (Xie et al., 1993, *J. Exp. Med.*, vol. 177, pp. 1779–1784, which disclosure is hereby incorporated by reference). Additional overlapping genomic fragments spanning about 72 kilobases (Kb) were cloned and characterized, as shown in FIG. 3. Cosmids were characterized by restriction mapping, Southern hybridization analysis and DNA sequence analysis, to demonstrate that this contig contains about 36 Kb of 5' upstream DNA and 36 Kb of the iNOS gene, including about three-fourths of the iNOS coding region (FIG. 3). The 3' genomic region remained uncloned even after screening about $3\times10^6$ genomic clones. The first six iNOS exons were mapped in a region of about 10 Kb. Within the 540 -UTR, the transcription initiation site was identified by primer extension and S1 nuclease analysis, and the IFN-γ-and LPS-inducible promoter function of this region was established by its incorporation into reporter constructs and their transfection and induction (Xie et al., 1993, cited elsewhere herein, which disclosure is hereby incorporated by reference).

Targeted disruption i.e., mutation, of the iNOS locus, was achieved using replacement vector piNOS-RV1 (FIG. 1). The replacement vector of the invention was designed to (1) enact the in-frame removal of exons 1–4; (2) delete the transcriptionally active 585 bp at the 3' end of the 5' untranslated region (Xie et al., 1993, cited elsewhere herein, which disclosure is hereby incorporated by reference); and (3) introduce an antisense PGK-driven neomycin resistance (NeO$^R$) gene as a positive selection marker.

The replacement vector was either singly transfected, as for the derivation of clone 5.23.133, or cotransfected along with the HSV thymidine kinase gene (TK), in the case of clone 6.16, into AB2.1 embryonic stem cells by electroporation (Reid et al., 1991, *Mol. Cell. Biol.*, vol. 11, pp. 2769–2777; and Davis et al., 1992, *Mol. Cell. Biol.*, vol. 12, pp. 2769–2776). Selection against the HSV-TK gene yielded a 3-fold enrichment of transformants. As described hereafter, clone 6.16 was identified after screening 937 clones, 439 individually and the remainder as pools of clones, by the polymerase chain reaction ("PCR"), of which 139 clones including clone 6.16 were also screened by Southern hybridization analysis. Clone 5.23.133 was identified after PCR screening of pools of clones totalling approximately 4400 clones, from which 144 clones, including clone 5.23.133, were additionally and individually screened by Southern hybridization analysis.

The disruption of the mouse iNOS gene i.e., introduction of a defect at its cognate chromosomal locus, occurred as a result of meiotic homologous recombination between the replacement vector nucleic acid sequence(s) i.e., selection marker, and the iNOS gene. Homologous recombination was carried out according to the method of Capecchi, M. R., 1989, *Science*, vol. 244, pp. 1288–92. Replacement vectors with overall homology between 6–14 kb (Hasty et al., 1991, *Mol. Cell. Biol.*, vol. 11, pp. 5586–91; Deng et al., 1992, *Mol. Cell. Biol.*, vol. 12, pp. 3365–71, which disclosures are hereby incorporated by reference), which are isogeneic with the target locus (Hasty et al., 1991, cited elsewhere herein; Riele et al., 1992, *Proc. Natl. Acad. Sci. USA*, vol. 89, pp. 5128–32, which disclosures are hereby incorporated by reference) and which enact exonic disruption or removal (Bradley et al., 1992, cited elsewhere herein, which disclosure is hereby incorporated by reference) have generally yielded the desired mutation with the highest efficiency. It is understood that the nucleic acid sequence incorporated into the vector(s) of the invention for disruption of the iNOS gene can comprise any known nucleic acid sequence (i.e., DNA fragment) provided it disrupts the natural mouse iNOS gene upon homologous recombination in a manner sufficient to prevent expression of inducible nitric oxide synthase and/or production of nitric oxide by inducible nitric oxide synthase. The preferred nucleic acid sequence is a DNA molecule encoding for a selectable marker gene, such as, neomycin resistance gene and/or the hygromycin resistance gene.

Figure 4:
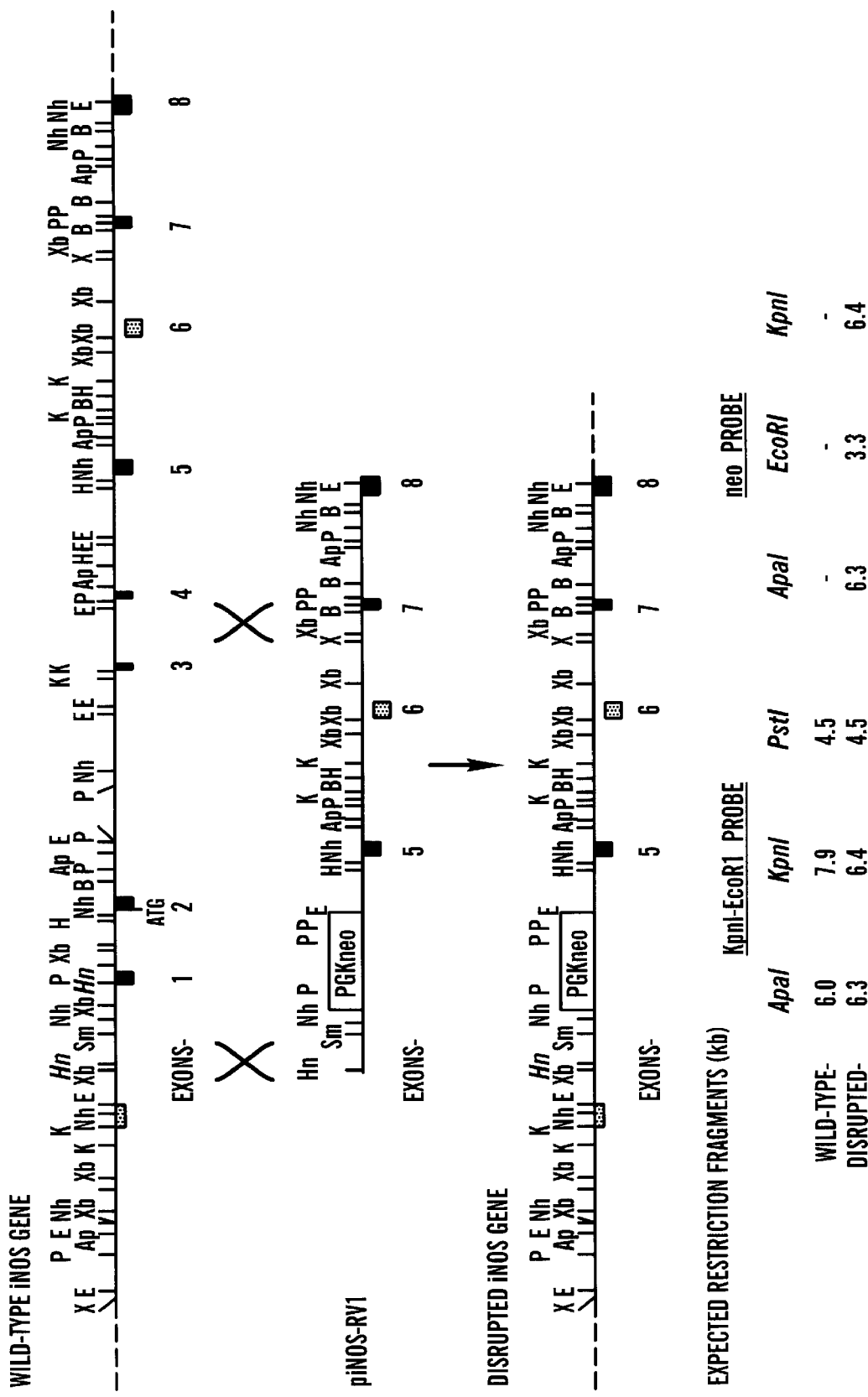
FIG. 4 shows the disruption of the iNOS gene in mouse embryonic stem cells [(wild-type iNOS Gene) shows a partial restriction map of the mouse inducible nitric oxide synthase genomic contig encompassing exons 1–; (disrupted iNOS Gene) Predicted structure of the mutated allele following homologous recombination; (Expected Restriction Fragments) Expected sizes of restriction fragments detected by flanking and Neo$^R$ probes; Positions of Southern probes for identification of allele-specific recombination are depicted. Arrowheads represent locations of 5' primers for PCR analysis].

With reference to FIG. 4, piNOS-RV1 incorporates about 6.7 Kb of genomic homology, is agouti 129/Sv strain-matched with its embryonic stem cell target locus and deletes exons 1–4 along with the transcriptionally active 3' 585 bp of the 5' flanking region ("UTR"). Transfection and selection of embryonic stem cells with this vector revealed an overall targeting efficiency of about 1 in 4400 G418-resistant clones tested (FIG. 4).

Transformed mouse cell lines congenitally deficient for the iNOS gene can be identified by any standard technique in the art, such as, for example, by DNA-DNA hybridization using probes comprising sequences that are homologous to the iNOS gene(s); presence or absence of "marker" gene function; and expression, or lack thereof, of the inserted sequences (iNOS) based on physical, immunological or functional properties. Once identified, these host cell lines are cultured under conditions which facilitate growth of the cells as will be apparent to one skilled in the art. Thereafter, stable transformants can be selected based upon the expression of one or more appropriate gene markers present or inserted into the replacement vector(s), such as, for example, G418 resistance. Expression of such marker genes should indicate that targeted disruption of the iNOS locus may have occurred. It is understood that any known gene marker in the art can be utilized herein. Such gene markers can be derived from cloning vectors, which usually contain a marker function. The preferred positive gene selection marker is the antisense PGK-driven neomycin resistance gene. A negative gene selection marker can in addition to the positive marker be included in the vector. The preferred negative gene selection marker is the HSV thymidine kinase gene.

Once transformants i.e., embryonic stem cell clones harboring the disrupted iNOS allele, were obtained, 12–15 of these transformed embryonic stem cells (clone 5.23.133) were microinjected into each of 3.5 day old C57B1/6 recipient blastocysts, which were then implanted in the uterus of pseudopregnant Tac:SW (fBR) foster females at 2.5–3.5 days post-coitum according to the method of Bradley, A., 1989, In "Teratocarcinomas and embryonic stem cells: a practical approach", E. J. Robertson, ed., Oxford, IRL Press, pp. 113–151, which disclosure is hereby incorporated by reference. Chimeric male pups somatically identified by coat color mosaicism for ES cell penetrance were bred at 6 weeks of age to C57B1/6 (black-coated) and 129/SvJ (agouti-coated) females. The dominant F1 agouti offspring were subsequently genotyped for germ-line transmission of the targeted iNOS allele by Southern blot hybridization analysis at the time of weaning (21 days postpartum). Male and female F1 transgenic offspring which possessed an altered single copy of the iNOS allele (heterozygous, iNOS$^-$/+) will be mated to obtain homozygosity for the mutation on an inbred 129/Sv or outbred C57B1/6 background. F2 generational iNOS$^{-/-}$ homozygous offspring, who will be shown to be fertile by breeding with wild type or heterozygous mates, will be used as founders for establishing colonies of iNOS-deficient mice.

The following Examples are provided to further illustrate the present invention.

EXAMPLE I

Preparation of Murine Embryonic Stem Cell Genomic Libraries

Recent evidence suggests that homologous genomic targeting in embryonic stem cells is strongly inhibited i.e., more than 100-fold, by subtle base pair differences in their genomic DNAs (Riele et al., 1992, cited elsewhere herein; and Deng et al., 1992, cited elsewhere herein, which disclosures are hereby incorporated by reference). Therefore, genomic libraries were constructed herein from embryonic stem cells grown in the absence of fibroblast feeder cell layers for the isolation of genes for subsequent targeting in the same line of embryonic stem cells. That is, either cES-J1 or cES-D3 cells were used to prepare genomic libraries following the in situ procedure according to Mudgett et al., 1990, Genomics, vol. 8, pp. 623–633, which disclosure is hereby incorporated by reference. Cosmid vector sCos-1 was chosen because it allows both vector and insert to be dephosphorylated to prevent concatemer formation, resulting in genomic libraries of better quality and quantity (i.e., as many as 5×10$^6$ clones per package)(Evans et al., 1989, Gene, vol. 79, pp. 9–20, which disclosure is hereby incorporated by reference). Three genomic libraries were constructed with different bacterial hosts to allow for a more representative and stable cloning of methylated and repetitive genomic sequences. HB101 (GIBCO) host cells were used to stably maintain sequence direct repeats more effectively than other bacterial strains. NM554 (STRATAGENE) host strain was used to allow more effective isolation of methylated genomic elements. The SURE host line (Stratagene) was used to stably maintain indirect repeats and allow isolation of methylated DNA. The three hosts were used to generate genomic libraries cES-I, CES-II, and cES-III, respectively.

EXAMPLE II

Isolation of Mouse iNOS Clones

The cES-J1 genomic library cES-I was thrice screened using a partial mouse iNOS cDNA encompassing nucleotides 200–1017 (GenBank accession number M87039; Xie et al., 1992, cited elsewhere herein, which disclosures are hereby incorporated by reference) according to the procedures of Sambrook et al., 1989, cited elsewhere herein, which disclosure is hereby incorporated by reference. The cDNA probe was chosen from a region encoding an NH$_2$-terminal portion of the iNOS protein. This region displays least homology with neural and endothelial cNOS cDNAs (Bredt et al., 1991, Nature, vol. 351, pp. 714–718; and Lamas, S., 1992, Proc. Natl. Acad. Sci. USA, vol. 89, pp. 6348–6352, which disclosures are hereby incorporated by reference). Along with the cDNA probe, high stringency hybridization conditions were used to reduce the possibility of isolating other NOS isoforms and related pseudogenes. Twelve primary clones were purified through secondary and tertiary screenings, and DNAs were prepared for the positive cosmids according to the procedures of Sambrook et al., 1989, cited elsewhere herein, which disclosure is hereby incorporated by reference. Of the twelve cosmids isolated, five were independent clones (represented by cosmids, cIN-2, cIN-6, cIN-7 and cIN-9 in FIG. 3).

Cosmid DNAs were digested with restriction endonucleases, electrophoresed on agarose gels, and hybridized with the partial 817 bp mouse iNOS cDNA insert according to the procedures of Sambrook et al., 1989, cited elsewhere herein, which disclosure is hereby incorporated by reference. Southern analysis indicated that all five clones were from the hybridizing genomic locus.

EXAMPLE III

Characterization of the Mouse iNOS Clones

Cosmid clones from the mouse iNOS locus were mapped with restriction endonucleases using the method of end-ordered partial digestion according to the procedure of Evans et al., 1989, Gene, vol. 79, pp. 9–20, which disclosure is hereby incorporated by reference. The location and extent of iNOS hybridizing regions of the inducible nitric oxide synthase gene were ascertained by hybridizing complete and end-ordered partial digestion of the cosmids with the mouse iNOS cDNA probe. The identity of the mouse iNOS gene was confirmed by nucleotide sequencing of exon regions according to the procedures of Sambrook et al., 1989, cited elsewhere herein, which disclosure is hereby incorporated by reference. Cosmid clones cIN-2, cIN-6, cIN-7 and cIN-9 contained exon nucleic acid sequences which were 100% identical to those contained in the partial murine iNOS cDNA. Therefore, these clones contained portions of the murine iNOS gene. Furthermore, these sequences were dissimilar to those for the rat neural constitutive nitric oxide synthase (cNOS) (Bredt et al., 1991, cited elsewhere herein, which disclosure is hereby incorporated by reference).

The mouse iNOS genomic contig (cosmids cIN-2, cIN-6, cIN-7, and cIN-9) was characterized with regard to vector-compatible restriction endonuclease sites, orientation, and exon locations using a combination of DNA sequencing, restriction digest and Southern hybridization analysis according to the procedures of Sambrook et al., 1989, cited elsewhere herein, which disclosure is hereby incorporated by reference. These analyses demonstrated that this contig contains approximately 38 kb of upstream DNA and 34 kb of the iNOS gene, extending some three-fourths into the iNOS coding region. Comparison with the transcriptionally active 1749-bp 5'-flanking region (UTR) of the iNOS gene (Xie et al., 1993, cited elsewhere herein, which disclosure is hereby incorporated by reference) revealed that all four cosmid clones (cIN-2, cIN-6, cIN-7 and cIN-9) contain the 5' promoter region. Comparison with the iNOS cDNA sequence (Xie et al., 1992, Science, vol. 256, pp. 225–228, which disclosure is hereby incorporated by reference) indicated that cosmid clones cIN-9 and cIN-6 contain exons 1 and 2, while cIN-2 and cIN-7 include at least exons 1–8.

EXAMPLE IV

Construction of iNOS Replacement Vectors

Replacement vector piNOS-RV1 (FIG. 1) contains a 1.034 Kb short arm adjoining a selectable Neo marker (P. Solloway, MIT) inserted into the XbaI site of the 5' promoter element, and a 6.7 Kb long arm, all contiguously assembled in the Bluescript SKII$^+$ vector (Stratagene). piNOS-RV1 was constructed according to the procedures of Sambrook et al., 1989, cited elsewhere herein, which disclosure is hereby incorporated by reference. Co-electroporation of piNOS-RV1 with herpes simplex thymidine kinase (HSV-TK) marker gene (P. Solloway, MIT) allowed for FIAU selection against non-targeted recombinants (Mansour et al., 1988, Nature, vol. 336, pp. 348–352; Capecchi, M. R., 1989, Science, vol. 244, pp. 1244–1292; Reid et al., 1991, Mol. Cell. Biol., vol. 12, pp. 2769–2777; and Davis et al., 1992, Mol. Cell. Biol., vol. 13, pp. 2769–2776, which disclosures are hereby incorporated by reference). The Neo gene is driven by the highly efficient mouse phosphoglycerate kinase-1 (PGK-1) promoter. The Neo gene was inserted into replacement vector piNOS-RV1 in a 3'–5' ("antisense") orientation to reduce the likelihood of cryptic transcriptional initiation generating a shortened, yet functionally active, iNOS protein. piNOS-RV1 facilitates insert of the Neo marker into the iNOS promoter and protein-encoding regions, thereby deleting the transcriptionally active 3' 715 bp of the 5' UTR and exons 1–4. The length of iNOS homology in piNOS-RV1 is about 7.7 kb.

More specifically, piNOS-RV1 contains a 1.034 Kb fragment possessing a 5' HincII site and a recessed 3'AG-repetitive end arising as a spontaneous event during cloning which deleted the original 3' Klenow-blunted XbaI site along with the immediate upstream 130-bp. This fragment was inserted into the HincII site of Bluescript SKII$^+$ (STRATAGENE) To this was added a HindIII-EcoRI PGK-neopA selectable marker inserted in an antisense orientation, an EcoRI-ligated 6.7 Kb long arm encompassing exons 5–8 (FIG. 1).

EXAMPLE V

Mutation of iNOS Gene in Murine Embryonic Stem Cells

Early passage (p11) (hrpt-) AB2.1ES cells were electroporated with NotI-linearized piNOS-RV1 in a BioRad Gene Pulser. Each electroporation was performed with 4×10$^6$ cells with 25 μg DNA in 0.8 ml electroporation buffer (Specialty Media) at 300 V, 250 μF, and plated into two 90 mm dishes with irradiated (7,500 Rad) SNL (STOneo$^r$) feeder fibroblasts (Robertson, 1987, In "Teratocarcinomas and embryonic stem cells," IRS Press, pp. 71–112, which disclosure is hereby incorporated by reference). Embryonic stem cell transformants were either selected with geneticin (200 μg/ml active G418) only or together with 0.2 μM of 1-[2' deoxy-2'-flouro-1-β-O-arabinofuranosyl]-5-iodouridine (FIAU), the latter when piNOS-RV1 was co-transfected with HSV-TKpA. Murine leukemia inhibitory factor (MuLIF) (ESGRO, Gibco BRL, Inc.) was also added daily during 10 days growth of resistant colonies. Selection with FIAU resulted in about 3-fold enrichment over G418 clones alone. Doubly resistant (G418- and FIAU) ES cell clones were isolated either by picking and growing individual colonies, or from pools of 15–25 colonies while those screened for single resistance (G418 only) were isolated as single clones from pools of between 15–25 colonies. Preparation of genomic DNA for PCR analysis of clones isolated via either method was undertaken as described by Laird et al., 1991, Nucleic Acids Res., vol. 19, pp. 4293, which disclosure is hereby incorporated by reference.

Figure 2:
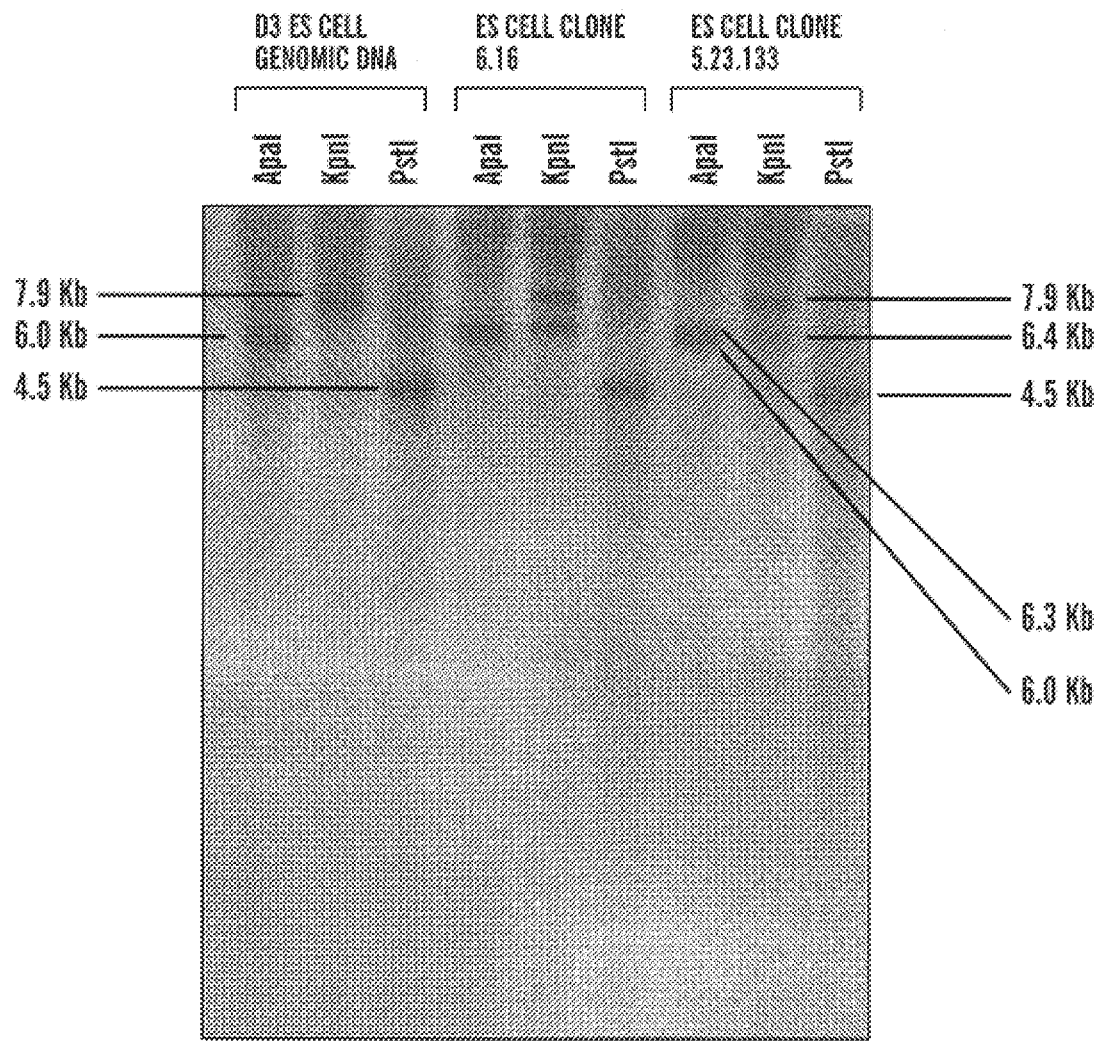
FIG. 2 shows a Southern hybridization analysis of an iNOS allele-targeted embryonic stem cell clone using the unique 5' flanking probe.

Oligonucleotide primers were designed and constructed to enable PCR assays for detecting the successful inactivation of the iNOS gene. U31 is a 5' primer 132 bp upstream of the piNOS-RV1 1.034 kb short arm (5'-GAGCAATGTGACAAAGCTCCTTCAGACTAGG-3') (SEQ.ID.NO.1). D28 is a 3' primer originating within PGK-neopA (5'-GTCTCCGACTAGAGCAAGAAGTCCG-3') (SEQ.ID.NO.2). By using these probes, only iNOS genes which have a Neo marker inserted in the correct location will yield the correct PCR product, i.e., short arm of the construct. PCR conditions for detecting iNOS targeted clones using these primers (200 nM) were 94° C. for 1.5 minutes, 40 cycles of 94° C. for 30 seconds, 62° C. for 45 seconds, 72° C. for 3 minutes, and 72° C. for 10 minutes. PCR conditions were 50 mM Tris, pH 8.5, 50 mM NaCl, 1.5 mM MgCl$_2$, and 2 mM DTT, and 1.25 U Taq enzyme. Clones exhibiting the desired 1.3 Kb amplificand underwent Southern hybridization using a $^{32}$P-labelled HincII-XbaI 1164-bp probe, and a 24 bp probe (IN24), 5'GTAGTGTTCCTG-GCTTATCCTAGA3'(SEQ.ID.NO.3), both of which were internal to the PCR primers to verify that the amplified DNA contained the short arm of piNOS-RV1. Genomic DNA from clones exhibiting the desired 1.3 kb amplificand were separately digested with restriction endonucleases. The DNA was transferred to Bio-Rad® ZetaProbe GT membranes and Southern hybridized with an EcoRl-BamHI digested Neo gene, and a 5' flanking novel sequence DNA probe. The 5' probe resides (5'–3') from the KpnI site to the EcoRI site (approximately 500 bp upstream of the RV1 site) (FIG. 4) and did not hybridize with mouse repetitive DNA (COT-1, Stratagene). Digestion of mouse genomic DNA with KpnI followed by hybridization with the 5' flanking probe yielded a single 7.9-kb wild type iNOS fragment, in contrast to the multiple hybridization signals observed for abundant repetitive DNA classes. Digestion and hybridization of genomic DNA from an iNOS targeted clone yielded two hybridizing fragments, one wild type 7.9 kb allele and one targeted 6.4 kb allele (FIG. 2).

EXAMPLE VI

Injection of iNOS Clones into Donor Blastocysts IFN-γ and Generation of Chimeras iNOS-targeted AB2.1 cell lines, as demonstrated by PCR and Southern hybridization analysis, were regrown in culture, their colony morphologies and growth characteristics determined microscopically, and the stability of their genotype again confirmed by Southern hybridization analysis. Targeted cell lines which grew normally and did not contain an abnormal proportion of differentiated cells were then separated from their feeder cells by treating the cell culture with trypsin, allowing the feeder cells to re-attach for 30–45 minutes, and removing the unattached embryonic stem cells according to the procedure of Robertson, E. J., 1987, cited elsewhere herein, which disclosure is hereby incorporated by reference. Embryonic stem cell clone 5.23.133 was injected into C57B1/6J recipient blastocysts in separate experiments according to the procedure of Bradley, A., In "Teratocarcinomas and embryonic stem cells," E. J. Robertson, ed. Oxford, IRL Press, pp. 71–112, 1987, which disclosure is hereby incorporated by reference. Injected C57B1/6J recipient blastocysts were reimplanted into uteri of 3 day pseudopregnant Ta:SW (fBR) female mice and allowed to develop to term. Progeny were screened initially by coat color chimerism. 17 chimeric male pups somatically identified by coat, color mosaicism (about 70–100%) for ES cell penetrance were identified. Mosaicism was further confirmed by PCR and Southern hybridization analysis performed on genomic DNA isolated from the tail samples of these mice. As the embryonic stem cell line AB2.1 is homozygous for the agouti (A) coat color gene, penetrance of embryonic stem cells into the injected (black coat color) C57B1/6J blastocyst gives rise to chimeric coat color mice.

EXAMPLE VII

Breeding Chimeric Mice

The chimeric coat color mice were outbred to C57B1/6J (black coated) and inbred to 129/J (agouti coated) female mice. Some of the progeny from the chimera X C57B1/J6 cross were expected to be agouti if the chimeric male had embryonic stem cell genetic material incorporated into its germline (i.e., agouti is dominant to black coat color). The chimera X 129/J crosses are expected to yield only agouti mice. These crosses will reveal whether male chimeric animals can transfer embryonic stem cell genetic information, including the disrupted iNOS allele, to their offspring.

To determine the iNOS genotypes, genomic DNA was purified from an approximately 1 cm length of the tail tip from each mouse after weaning. The genomic DNA was isolated as described by Laird et al., 1991, cited elsewhere herein, which disclosure is hereby incorporated by reference, followed by phenol and phenol:chloroform extractions and ethanol precipitation. PCR and Southern hybridization analyses were used to identify offspring which contained the disrupted iNOS allele. These transgenic offspring are heterozygous for the iNOS disruption. Southern hybridization analysis was used to confirm that the structure of the altered iNOS gene was identical to that predicted, and previously characterized in the iNOS targeted clones. Both transgenic heterozygous and non-transgenic mouse tail genomic DNAs were digested with KpnI and subsequently hybridized with 5' flanking DNA probes to confirm the transgenic iNOS structure as was demonstrated for ES clones 6.16 and 5.23.133 (FIG. 2).

EXAMPLE VIII

Breeding Heterozygous Mice and Generation of iNOS-deficient Transgenic Mice Male and female transgenic mice which contain one copy of the altered iNOS allele (heterozygous mice) will be mated with each other to generate mice in which both copies of the iNOS gene consist of a targeted, altered transgenic iNOS gene. It is predicted from Mendelian genetic principles that one in four of the mouse embryos will be homozygous for the altered iNOS gene. Surviving offspring will be genotyped by Southern hybridization as previously described (FIG. 2), and the percentages of the offspring mice will be determined for targeted iNOS $^{-/-}$ homozygosity, wild-type iNOS $^{+/+}$ homozygosity, and iNOS $^{-/+}$ heterozygosity. $F_2$ generational iNOS$^{-/-}$ homozygous offspring, if shown to be fertile by breeding with wild type or heterozygous mates, will be used as founders for establishing colonies of iNOS-deficient mice.

Male and female $F_1$ transgenic offspring which possess an altered single copy of the iNOS allele (heterozygous, iNOS$^-$/$^+$) will be mated to obtain homozygosity for the mutation on an inbred 129/Sv or outbred C57B1/6 background.

EXAMPLE IX

Uses of iNOS-deficient Transgenic Mice

As sufficient numbers of iNOS-deficient animals accumulate via matings of fertile male and female mutant founder mice, their susceptibility to tumorigenic challenge, autoimmunity, infection and septic shock can be evaluated. Infectious agents which can be tested using these mice include, without limitation, *Mycobacterium tuberculosis, Mycobacterium leprae*, ectromelia and *influenza* A viruses, *Listeria monocytogenes, Leishmania donovani*, all demonstrably susceptible to inhibition by iNOS (Nathan et al., 1991, cited elsewhere herein; and Karupiah et al., 1993, *Science*, vol. 261, pp. 1445–1447, which disclosures are hereby incorporated by reference). It is understood that microbial challenge is not limited to the above named pathogens. Mice highly susceptible to these agents by virtue of their iNOS deficiency would be-useful as hosts in which to test new therapies, such as pharmacologic agents, with the least possible perturbation of their immune system and other physiologic responses. Such mice in particular could provide a much-needed small animal model for the rapid screening of compounds with anti-mycobacterial efficacy.

Such mice will also be useful to evaluate the contribution of iNOS to septic shock, for example, as it is modelled by the injection of bacterial lipopolysaccharide (LPS). For this, the survival of iNOS-deficient mice can be compared to the survival of wild-type mice following the injection of various doses of LPS.

Autoimmune disorders in which a pathogenic role for iNOS is implicated include arthritis (McCartney-Francis et al., cited elsewhere herein, which disclosure is hereby incorporated by reference) insulin-dependent diabetes mellitus (IDDM) (Kleeman et al., 1993, *FEDS Lett.*, vol. 32, pp. 9–12, which disclosure is hereby incorporated by reference), experimental autoimmune encephalomyelitis (EAE) (MacMicking et al., cited elsewhere herein, which disclosure is hereby incorporated by reference) and murine systemic lupus erythematosus (SLE). Backcrosses of iNOS $^{-/-}$ mice with strains well-characterized for disease susceptibility (i.e., B10.RIII, NOD, and MRL-1 pr/1 pr strains for CIA, IDDM and SLE, respectively) will elucidate whether iNOS is obligate for the development of these autoimmune disorders, which cannot satisfactorily be answered with currently available inhibitors.

It should be understood that the foregoing embodiments are provided for purpose of illustration only and not limitation, and that all such modifications or changes which occur to persons skilled in the art are deemed to be within the spirit and scope of the present invention.

What is claimed:

1. A transgenic mouse whose somatic and germ cells comprise a homozygous disrupted inducible nitric oxide synthase gene, said disruption sufficient to inhibit the production of nitric oxide by inducible nitric oxide synthase, said disrupted gene being introduced into said mouse or an ancestor of said mouse at an embryonic stage, wherein said mouse demonstrates an increased susceptibility to bacterial or viral infection and a decrease in susceptibility to sepsis as compared to a wild type mouse.

2. The mouse of claim 1, wherein said mouse exhibits an absence of inducible nitric oxide synthase.

3. The mouse of claim 1, wherein said mouse transmits said disrupted gene to its homozygous offspring which demonstrate an increased susceptibility to bacterial or viral infectious agents and a decreased susceptibility to sepsis as compared to a wild type mouse.

4. A transgenic mouse whose somatic and germ cells comprise a heterozygous disrupted inducible nitric oxide synthase gene, said disrupted gene being introduced into said mouse or an ancestor of said mouse at an embryonic stage, and wherein said disruption is sufficient to inhibit the production of nitric oxide by inducible nitric oxide synthase such that the mouse demonstrates a decreased susceptibility to sepsis as compared to a wild type mouse.

5. The mouse of claim 4, wherein said mouse transmits said disrupted gene to its heterozygous offspring which demonstrate a decreased susceptibility to sepsis as compared to a wild type mouse.

6. The mouse of claim 1 or 4 wherein said disruption gene has been introduced into said mouse at an embryonic stage by microinjection.

7. The mouse of claim 1 or 4 wherein said disrupted gene has been introduced into an ancestor of said mouse at an embryonic stage by microinjection.

8. The mouse of claims 1 or 4, wherein said disruption is generated by homologous recombination between the endogenous inducible nitric oxide synthase gene and a vector comprising an inducible nitric oxide synthase gene containing a disruption that prevents production of inducible nitric oxide synthase.

9. The mouse of claim 8, wherein said vector is piNOS-RV1.

10. A method of producing a heterozygous mouse whose somatic and germ cells contain a gene coding for a disrupted mouse inducible nitric oxide synthase, comprising:

(a) providing a gene coding for a disrupted mouse inducible nitric oxide synthase, said disruption having occurred at a level sufficient to prevent expression of mouse inducible nitric oxide synthase and/or production of nitric oxide by mouse inducible nitric oxide synthase;

(b) introducing said gene into the blastocyst of an embryo;

(c) transplanting the embryo into a pseudopregnant mouse and allowing said blastocyst to develop to term;

(d) identifying a mouse which carries said disruption in one allele, said mouse exhibiting a decrease in susceptibility to sepsis as compared to wild type mice.

11. The method of claim 10, wherein said introducing step is by microinjection of the blastocyst.

12. A method of producing a homozygous mouse whose somatic and germ cells contain a gene coding for a disrupted mouse inducible nitric oxide synthase, comprising:

(a) providing a gene coding for a disrupted mouse inducible nitric oxide synthase, said disruption having occurred at a level sufficient to prevent expression of mouse inducible nitric oxide synthase and/or production of nitric oxide by mouse inducible nitric oxide synthase;

(b) introducing said gene into a blastocyst;

(c) transplanting said embryo into a pseudopregnant mouse and allowing said blastocyst to develop to term;

(d) identifying a mouse which carries said disruption;

(e) interbreeding said mouse of step (d) with a second mouse carrying said disruption; and (f) identifying a mouse which carries said disruption in both alleles, said mouse exhibiting a phenotype characterized by the substantial absence of expression of mouse inducible nitric oxide synthase and/or production of nitric oxide mouse by inducible nitric oxide synthase and by an increased susceptibility to bacterial or viral infectious agents, or a decreased susceptibility to sepsis.

13. A method of testing the susceptibility of an inducible nitric oxide synthase deficient mouse to bacterial or viral infectious agents comprising challenging the mouse of claim 1 with said agents, and evaluating the effect of such challenge.

* * * * *